US009045795B2

(12) United States Patent
Ball et al.

(10) Patent No.: US 9,045,795 B2
(45) Date of Patent: Jun. 2, 2015

(54) METHODS TO CONTROL DISSOLVED GAS

(71) Applicant: LIFE TECHNOLOGIES CORPORATION, Carlsbad, CA (US)

(72) Inventors: James Ball, Ledyard, CT (US); David Kupec, San Francisco, CA (US); David Marran, Durham, CT (US); Jon A. Hoshizaki, Cupertino, CA (US)

(73) Assignee: Life Technologies Corporation, Carlsbad, CA (US)

( * ) Notice: Subject to any disclaimer, the term of this patent is extended or adjusted under 35 U.S.C. 154(b) by 15 days.

(21) Appl. No.: 13/802,610

(22) Filed: Mar. 13, 2013

(65) Prior Publication Data

US 2014/0272980 A1 Sep. 18, 2014

(51) Int. Cl.
*C12Q 1/68* (2006.01)

(52) U.S. Cl.
CPC ......... *C12Q 1/68* (2013.01); *Y10T 436/143333* (2015.01); *C12Q 1/6883* (2013.01)

(58) Field of Classification Search
CPC ...................................................... C12Q 1/68
USPC ........................................................ 435/6.1
See application file for complete search history.

(56) References Cited

U.S. PATENT DOCUMENTS

| 5,229,297 | A * | 7/1993 | Schnipelsky et al. ........... 436/94 |
| 5,475,610 | A * | 12/1995 | Atwood et al. ................ 700/269 |
| 7,049,645 | B2 * | 5/2006 | Sawada et al. ................ 257/292 |
| 2014/0057268 | A1 * | 2/2014 | Tanner et al. ................ 435/6.12 |

OTHER PUBLICATIONS

"Systec MINI—Vacuum Degassing Chamber", *IDEX Health & Science LLC—Product Data Sheet*, 2009, 2 pages.

\* cited by examiner

*Primary Examiner* — Ardin Marschel

(57) ABSTRACT

A method of sensing nucleotide reactions includes flowing at least one nucleotide solution from a container of at least two containers of a sensor system. The sensor system includes a sensor sensitive to a byproduct of nucleotide incorporation. Each container of the at least two containers includes a different nucleotide solution. The sensor system enters an idle mode after flowing. The method further includes cycling the at least two containers through at least two cycles. Each cycle includes depressurizing the at least two containers for a first period and pressurizing the at least two containers for a second period. The method also includes pressurizing the at least two containers when the sensor system enters an active mode.

10 Claims, 4 Drawing Sheets

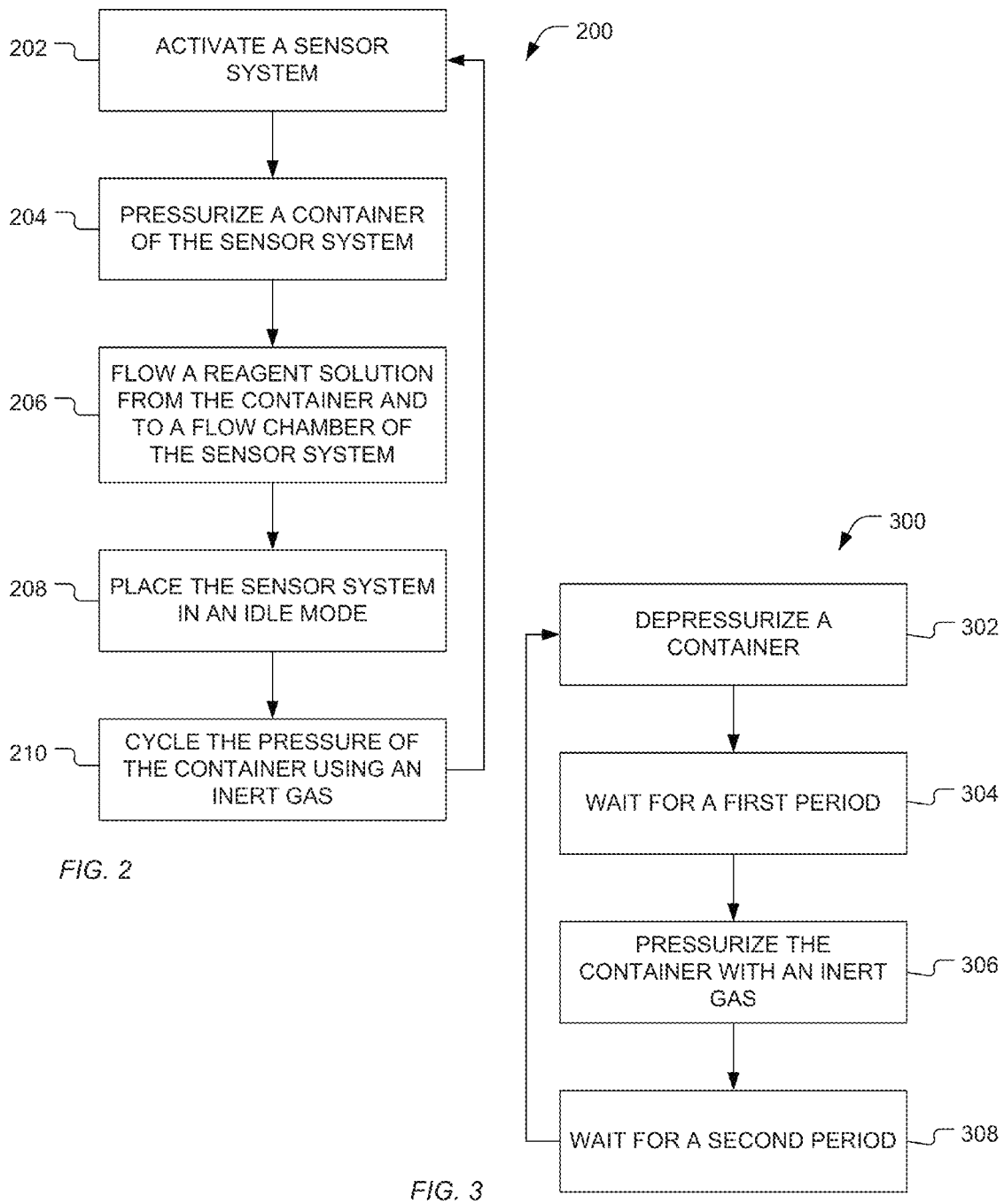

METHODS TO CONTROL DISSOLVED GAS

FIELD OF THE DISCLOSURE

This disclosure, in general, relates to systems and methods for reducing dissolved gas in a sensor system.

BACKGROUND

Sensors for measuring a chemical or biological response are increasingly relying on measurement of ion concentration or pH. More recently, sensor systems for detecting reactions in molecular biology use sensors for measuring ionic concentration or pH. In particular, sensor systems measuring ionic concentration or pH have been used for quantitative polymer chain reaction (PCR) and genetic sequencing.

SUMMARY

In a first aspect, a method of sensing nucleotide reactions includes flowing at least one nucleotide solution from a container of at least two containers of a sensor system. The sensor system includes a sensor sensitive to a byproduct of nucleotide incorporation. Each container of the at least two containers includes a different nucleotide solution. The sensor system enters an idle mode after flowing. The method further includes cycling the at least two containers through at least two cycles. Each cycle includes depressurizing the at least two containers for a first period and pressurizing the at least two containers for a second period. The method also includes pressurizing the at least two containers when the sensor system enters an active mode.

In a second aspect, an apparatus includes at least two containers. Each container of the at least two containers includes a different nucleotide solution. The apparatus further includes a degasser in fluid communication with a container of the at least two containers. The degasser is to receive a nucleotide solution from the container of the at least two containers and is to separate dissolved gas from the nucleotide solution received from the container of the at least two containers. The apparatus further includes a flow chamber in fluid communication with the degasser. A sensor is disposed within the flow chamber. The sensor is sensitive to a byproduct of nucleotide incorporation.

BRIEF DESCRIPTION OF THE DRAWINGS

The present disclosure may be better understood, and its numerous features and advantages made apparent to those skilled in the art by referencing the accompanying drawings.

FIG. 2 and FIG. 3 include block flow illustrations of exemplary methods.

The use of the same reference symbols in different drawings indicates similar or identical items.

DETAILED DESCRIPTION

Figure 1:
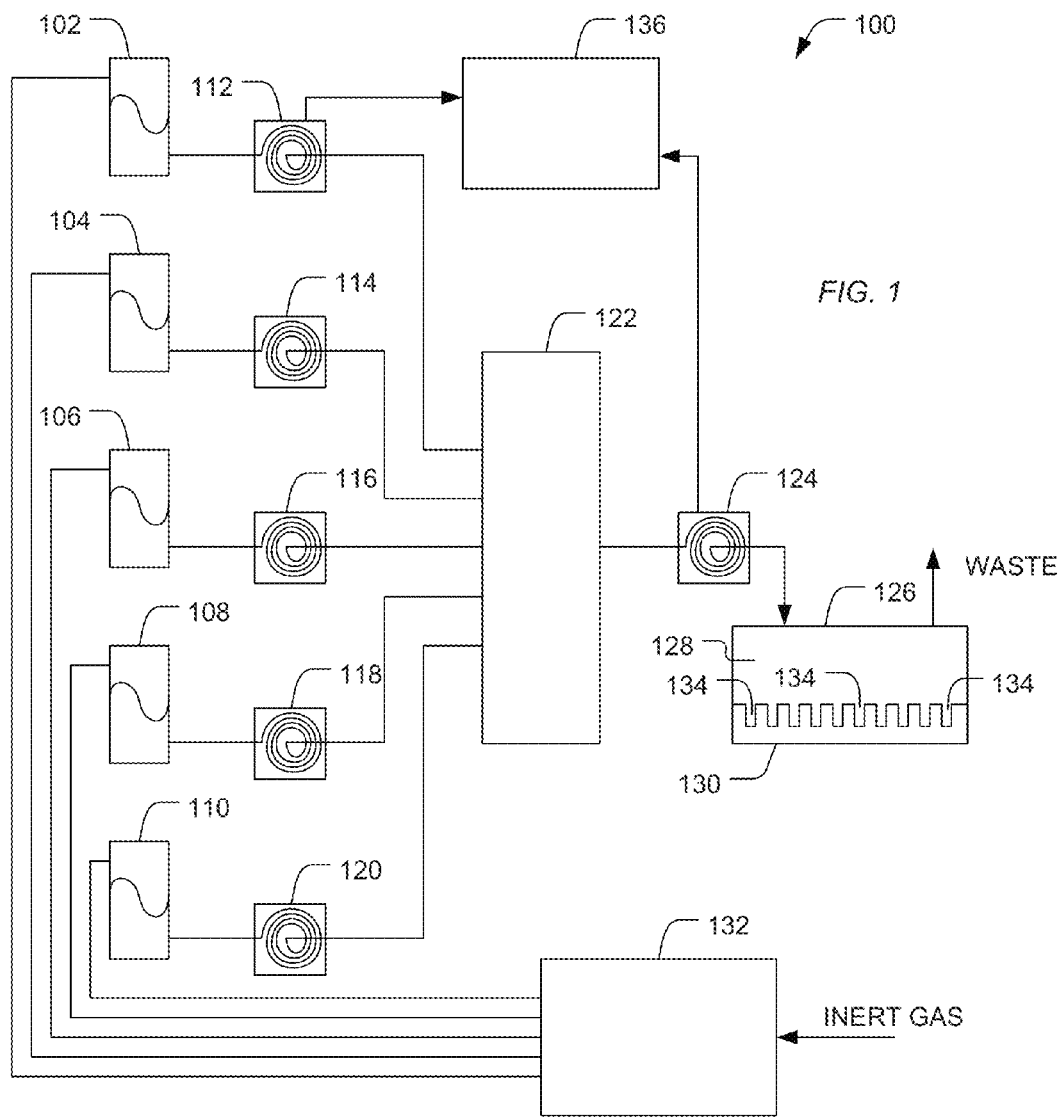
FIG. 1 includes an illustration of an exemplary sensor system.

In an exemplary embodiment, a plurality of containers including reagent solutions is connected to a flow control device that selectively provides a reagent solution from a container to a sensor device. The sensor device includes a flow chamber. The sensor device can include an array of sensors and an array of reaction chambers or wells in fluid communication with the flow chamber. The reaction chambers or wells of the array of reaction chambers or wells are operatively coupled to sensors of the sensor array. In particular, the sensors of the sensor array are sensitive to ionic concentration or pH. For example, a sensor of the sensor array can include a field effect transistor (FET), such as a chemically sensitive FET (chemFET), for example, an ion sensitive field effect transistor (ISFET). The reagent solutions can flow out of the flow chamber to a waste port or waste container. The system can include one or more degassers fluidically coupled between containers of the plurality of containers and the flow control device. In another example, a degasser can be fluidically coupled between the flow control device and the flow chamber of the sensor device. Optionally, the system can include a vacuum device operatively coupled to an outer chamber of the one or more degassers.

In a further example, a method for detecting a chemical or biological reaction includes flowing a reagent solution from a container through a flow control device to a flow chamber of a sensor device. The sensor device can include a plurality of reaction chambers in fluid communication with the flow chamber. Sensors of the sensor device can be operatively coupled to the plurality of reaction chambers and can detect products or byproducts of chemical or biological reactions. Following flowing, the system can enter into an idle mode. The method can further include cycling a pressure within the reagent solution container when the system is in idle mode. Cycling can include depressurizing the reagent solution container for a first period and re-pressurizing the container using an inert gas for a second period. When the sensor system is again activated or placed in an active node in preparation for flowing the reagent solution or detecting a chemical or biological reaction, a reagent solution container can be re-pressurized using the inert gas. In an example, the first period is at least twice the second period.

In a particular example, the systems and methods find use in measuring or detecting chemical or biological reactions that produce very small changes in ionic concentration or pH. Exemplary systems utilize small reaction chambers having volumes in a range of 0.01 fL to 10 pL. The sensor can measure ionic concentration or pH. For example, the sensor can detect a change in pH of 0.01 to 0.2 or have resolution in a range of 0.001 to 0.02 pH units. It has been discovered that such sensitive measurement of ionic concentration or pH can be influenced by even small amounts of dissolved carbon dioxide either dissolved as a result of the preparation of reagent solutions or diffusion through container walls when the sensor system sits idle, particularly at a near neutral pH, e.g., a pH in a range of 6 to 8. Such a problem increases noise within the system and increases errors associated with detecting the incorporation of nucleotides. The proposed systems and methods mitigate this discovered problem and improve signal-to-noise ratio and accuracy of the sensor measurement.

FIG. 1 includes an illustration of an exemplary sensor system 100 that includes one or more reagent containers 102, 104, 106, 108, and 110. The reagent containers (102, 104, 106, 108, and 110) are fluidically connected to a flow control device 122. The flow control device 122 selectively provides reagent solutions from the reagent containers (102, 104, 106, 108, and 110) to a sensor device 126. The sensor device 126 includes a flow chamber 128 in fluid communication with a plurality of reaction chambers 134 associated with a sensor array 130. In an example, the array of sensors 130 includes field effect transistors, such as chemFETs, e.g., ion sensitive field effect transistors (ISFET). In particular, the array of sensors 130 can be sensitive to ionic concentration or, for example, pH. In an example, the reaction chamber 134 has a volume in a range of 0.01 fL to 10 pL, such as a range of 0.01 fL to 1 pL, a range of 0.05 fL to 0.5 pL, a range of 0.1 fL to 100 fL, or a range of 0.1 fL to 10 fL. In an embodiment, such sensors can be used to detect nucleotide incorporation or can be used for quantitative analysis of gene expression (e.g., qPCR).

The reagent containers (102, 104, 106, 108, and 110) can include reagent or wash solutions useful for facilitating a reaction to be detected in the sensor device 126. In a particular example, the containers can include nucleotide solutions, each including an individual nucleotide species (e.g., T, A, C, or G) and one or more wash solutions.

One or more degassers can be placed in fluid communication between the containers and the flow control device 122 or between the flow control device 122 and the sensor device 126. For example, a degasser 112 can be in fluid communication between the container 102 and the flow control device 122. In another example, a degasser 114 is in fluid communication between the container 104 and the flow control device 122. In a further example, a degasser 116 is in fluid communication between the container 106 and the flow control device 122, a degasser 118 is in fluid communication between the container 108 and the flow control device 122, or a degasser 120 is in fluid communication between the container 110 and the fluid control device for flow control device 122. In an additional example, a degasser 124 is in fluid communication between the flow control device 122 and the sensor device 126. Each degasser can include a membrane defining a flow path and a chamber defined outside of the membrane and inside of a housing of the degasser.

The system 100 can further include a vacuum device 136. The vacuum device 136 can be connected to one or more of the degassers (112, 114, 116, 118, 120, or 124). Alternatively, the degassers (112, 114, 116, 118, 120, or 124) can be open to the atmosphere or can include a check valve that permits one-way flow from within the degasser to outside of the degasser. The vacuum system 134 can be in fluid communication with the chamber inside the degasser. In a further example, the degassers can be purged with an inert gas, such as helium or nitrogen.

Each of the containers 102, 104, 106, 108, or 110 can be connected to an inert gas system 132. In an example, the inert gas system 132 pressurizes each of the containers (102, 104, 106, 108, or 110) to provide a driving force to drive fluid from the containers to the flow control device 122. In addition, when the system is idle, the inert gas system 132 depressurizes the containers (102, 104, 106, 108, or 110) and periodically re-pressurizes the containers with an inert gas. For example, the inert gas can include a noble gas, such as helium, or an inert diatomic gas, such as nitrogen.

When in an active mode, the sensor system 100 pressurizes the containers 102, 104, 106, 108, or 110 and the flow control device 122 selectively permits flow from one or more of the containers to the sensor device 126. In the example of a sequencing system, solutions including individual nucleotides species can be sequentially provided to the sensor device 126 by the flow control device 122. A wash solution can be provided by the flow control device 122 intermediately between the flow of each reagent solution including a nucleotides species. The sensor device 126 can include within one or more reaction chambers 134 template nucleic acids to which a nucleotide within a reagent solution can hybridize. A byproduct of such a reaction can influence the pH of the microenvironment within the reaction chamber, which can in turn be sensed by a sensor associated with the reaction chamber 134.

Depending on the nature of the reaction taking place within the reaction chamber 134, the ion concentration or pH change in the microenvironment defined by the reaction chamber 134 is small. For example, the sensor can be configured to measure a pH change within a range of less than 0.5 pH units, such as less than 0.3 pH units, or less than 0.2 pH units at a pH in a range of 6 to 8. In particular, the pH sensor may have a resolution for measuring pH within a range of 0.005 to 0.05, such as a range of 0.005 to 0.02, or even a range of 0.01 to 0.02 pH units.

Such a system is sensitive to small fluctuations in pH, particularly those resulting from changes in the reagent solutions or wash solution. As such, cycling pressure when the system is idle, degassing reagent solutions prior to entry into the sensor device, or a combination thereof, reduces measurement errors by the sensor device 126 associated with nucleotide incorporation or primer extension.

In particular, the pressure within the containers can be cycled when the system is in an idle mode. In an example illustrated in FIG. 2, a method 200 includes activating a sensor system, as illustrated at 202. Activating the sensor system can include supplying a sensor device for the sensor system or performing calibration functions to prepare the system for performing a chemical or biological reaction. In an example of a genetic sequencing system, a chip device including a flow cell can be applied within the system and fluidically connected to a flow control device that can selectively flow nucleotide solutions and a wash solution from a set of containers to the flow cell.

The containers including reagent solutions, such as nucleotide solutions or a wash solution, can be pressurized using an inert gas, as illustrated at 204. In an example, the pressure within the containers is used to drive reagent solution flow that is controlled by the flow control device.

The flow control device can permit a solution to flow from one of the containers and selectively provide the solution to a flow chamber of the sensor device, as illustrated at 206. In a genetic sequencing device, the flow control device can selectively permit a nucleotide solution including a species of nucleotide to flow through the flow chamber of the sensor device followed by sequential flow of another nucleotide solution. Optionally, a wash solution can be provided to the flow chamber of the sensor device between flows of nucleotide solution.

Once a test or run is complete, the sensor system can be placed in idle mode, as illustrated at 208. In idle mode, reagent solutions are not drawn from the one or more of the containers. Optionally, the sensor device can be removed, particularly in a chip-based sequencing device.

Once the system is in an idle mode, the inert gas system can cycle pressure within the containers that include reagent solutions or wash solutions, as illustrated at 210. In particular, the inert gas system can cycle the pressure of the containers at least twice within an idle period, such as at least 5 times, at least 10 times, at least 20 times, or even at least 100 times. To perform another test, the system can be activated again, as illustrated at 202.

To cycle pressures within the containers, a method 300 illustrated in FIG. 3 includes depressurizing a container, as illustrated at 302. In an example, the container can be depressurized to atmospheric pressure, such as 0 PSIG. In another example, the container can be depressurize to a pressure not more than 50% of the pressure of the container during an active run of the system, such as not more than 35% of the active pressure or even not more than 20% of the active pressure.

A container can be held at the pressure, as illustrated at 304, for a first period. In an example, the first period can be in a range of 1 min. to 60 min, such as a range of 1 min to 30 min, or a range of 5 min to 20 min.

Following the first period, the inert gas system can re-pressurize a container, as illustrated at 306. For example, the inert gas system can re-pressurize a container to a pressure in a range of 60% to 150% of the pressure utilized during an active run, such as a range of 75% to 115% of the active run pressure, or range of 85% to 105% of the active run pressure, or approximately 100% of the active run pressure.

Pressure within the container can be held for a second period, as illustrated at 308. In an example, the second period can be in a range of 5 seconds to 20 min such as a range of 5 seconds to 10 min, a range of 5 seconds to 5 min, a range of 5 seconds to 1 min., or a range of 10 seconds to 30 seconds. In particular, a ratio of the first period to the second period can be in a range of 10:1 to 100:1, such as a range of 15:1 to 75:1, a range of 20:1 to 50:1, or even a range of 25:1 to 45:1, or approximately 30:1 (first period: second period).

Following the second period, the container can be again depressurized, as illustrated at 302 and the method repeated, each repeat of the method constituting a cycle.

Figure 6:
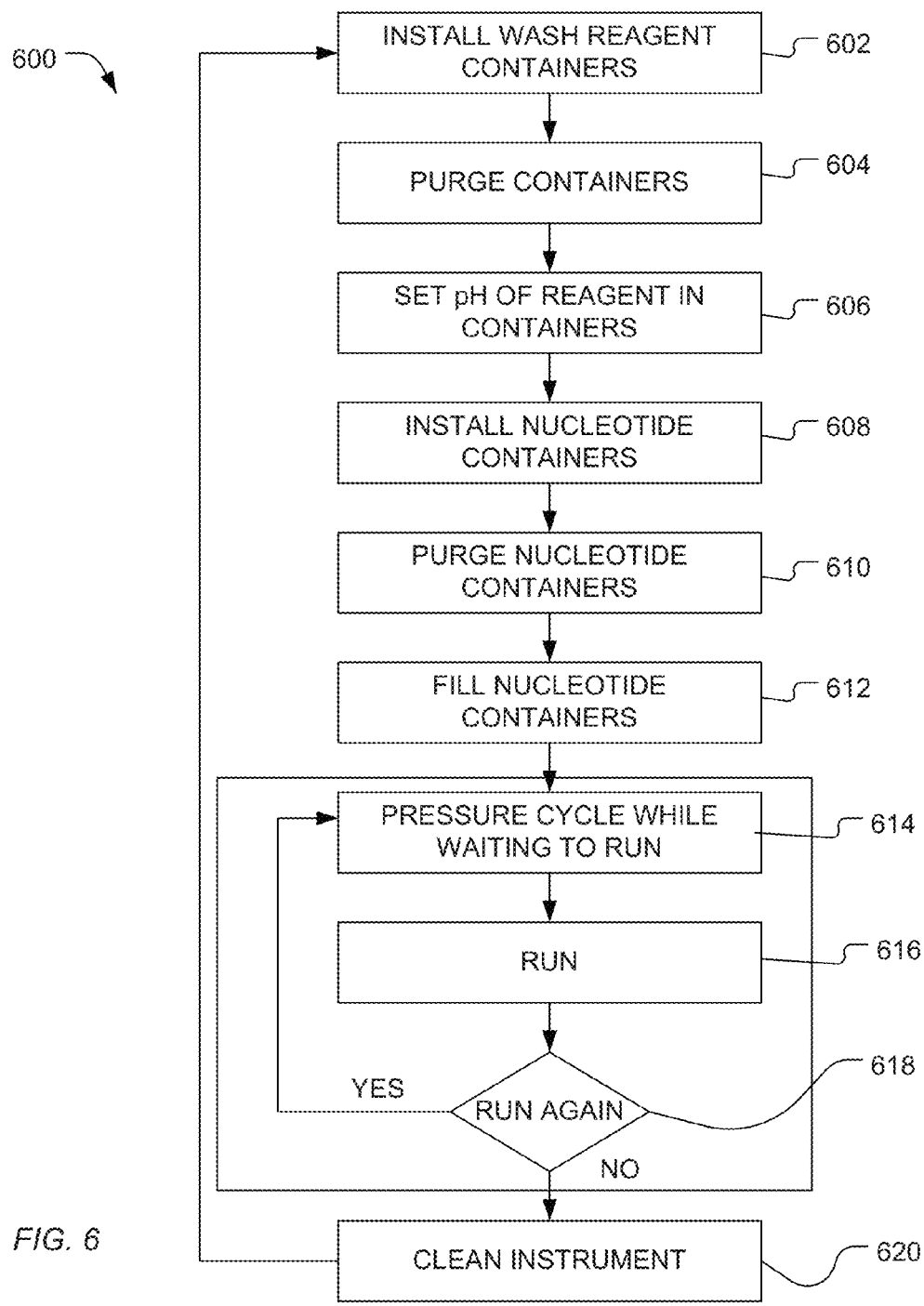
FIG. 6 includes a block flow illustration of an exemplary method.

In particular, as illustrated in FIG. 6, a method 600 includes installing wash reagent containers, as illustrated at 602. The wash reagent containers can include a wash reagent prepared as part of configuring the sequencing device. The wash reagent in the containers can be installed within the system and purged, as illustrated 604, with an inert gas, such as helium or diatomic nitrogen.

Optionally, the pH of reagents in the wash containers can be measured. In a particular example, the pH can be adjusted, as illustrated at 606. Such adjustment can be made using a pH adjusting solution.

The method 600 further includes installing nucleotide containers including nucleotide reagents, such as concentrated nucleotide reagents, as illustrated 608. For example, four different nucleotide solutions, each including a different nucleotide (e.g., A, T, G, or C) can be coupled to the sequencing system. The containers can be purged with an inert gas, such as helium or diatomic nitrogen, as illustrated 610. Optionally, the nucleotide containers can be filled using a buffered solution, such as the reagent solution, as illustrated at 612.

Following the initiation of the sequencing system, the system can cycle the pressure while waiting to run, as illustrated 614. For example, the system can use a pressure cycle as described above. At the direction of a user or based on a time or other automatic system, a run can be initiated, as illustrated 616. The run generally includes sequentially drawing the nucleotide solutions with intermediate draws of wash reagent and applying the solutions and reagents over a sequencing device.

Once the run is complete, the system can determine whether an additional run is going to take place, as illustrated at 616. If the additional run is to be performed, the system can pressure cycle while waiting to run, as illustrated 614. If the system has completed the desired runs, the instrument can undergo a cleaning process, as illustrated 620. Following the cleaning process, the system can be started again with the installation of wash reagent containers, as illustrated 602.

Figure 4:
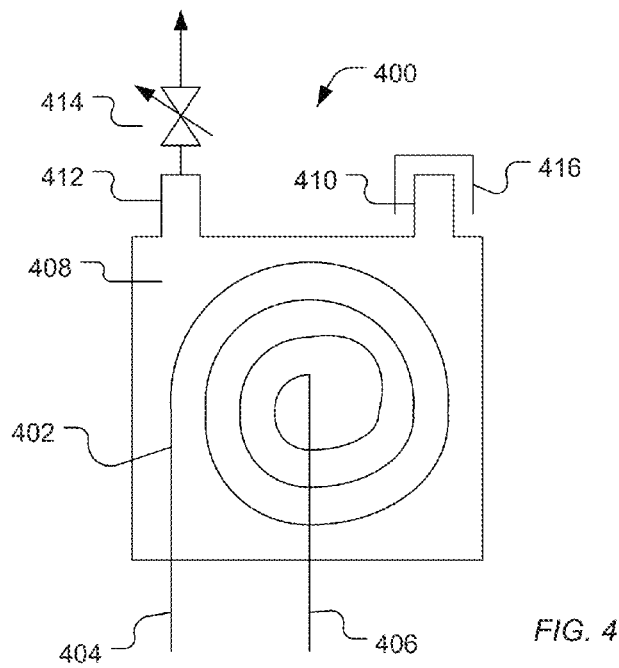
FIG. 4 includes an illustration of exemplary degasser module.

The system can include degassers in fluid communication between containers and a flow control device or between a flow control device and a sensor device. In an example illustrated in FIG. 4, a degasser 400 includes a membrane 402 within a chamber 408 defined by a housing 420. The membrane 402 defines a flow path for fluid flowing from inlet 404 to outlet 406.

In particular, the membrane 402 includes a gas permeable tube coiled within the chamber 408. An exemplary membrane 402 can be formed of a gas permeable polymeric material, such as a fluoropolymer including a perflourinated polymer or a perflourinated copolymer, polyphenol sulfide (PPS), polyether ether ketone (PEEK) or derivatives thereof, or any combination thereof. An exemplary fluoropolymer includes polytetrafluoroethylene (PTFE), fluorinated ethylene propylene (FEP) copolymer, a copolymer of tetrafluoroethylene, hexafluoropropylene, and vinylidene fluoride (THV), a copolymer of tetrafluoroethylene and perfluoro methylvinylether (PFA or MFA), a fluoropolymer having a fluorinated oxolane in its backbone, perfluoroether, or any combination thereof.

The chamber 408 can include one or more ports, such as ports 410 or 412. In an example, the port 412 is an effluent port and can be connected to a vacuum system. As illustrated, the port 412 may include a check valve 414 preventing flow from entering the chamber through the port 412. The port 410 can be connected to a vacuum pressure controller or purged with an inert gas, such as helium or nitrogen. Alternatively, the port 410 can be left open to atmosphere or can be capped, as illustrated with cap 416.

In particular, it was found that a method that includes cycling pressure of the containers using an inert gas reduced pH changes, including pH drift, and provides improved buffering over an extended period. The use of the degassing further stabilizes and reduces fluctuations within the solution, leading to reduced nucleotide incorporation measurement errors. A combination of such aspects provides both long-term and short-term stability of the pH and dissolved gas leading to improved sequencing, particularly for systems operating at a pH in a range of 6 to 8 or systems including a heated sequencing device. In fact, the proposed system provides the ability to tune pH by varying the cyclical purge profile. In particular, the pH influences enzyme activity and thus influences signal in the system. Low pH, in particular, can reduce enzyme activity.

EXAMPLE

Five reagent solutions are treated by cycling pressures over a 20 hour period. The reagent solutions include four nucleotide solutions and a wash solution. The respective containers are depressurized to atmospheric pressure for 10 minutes and are re-pressurized with nitrogen for 20 seconds. This cycle is repeated over a 20 hour period. A similar set of solutions is held at atmospheric pressure for comparison.

Figure 5:
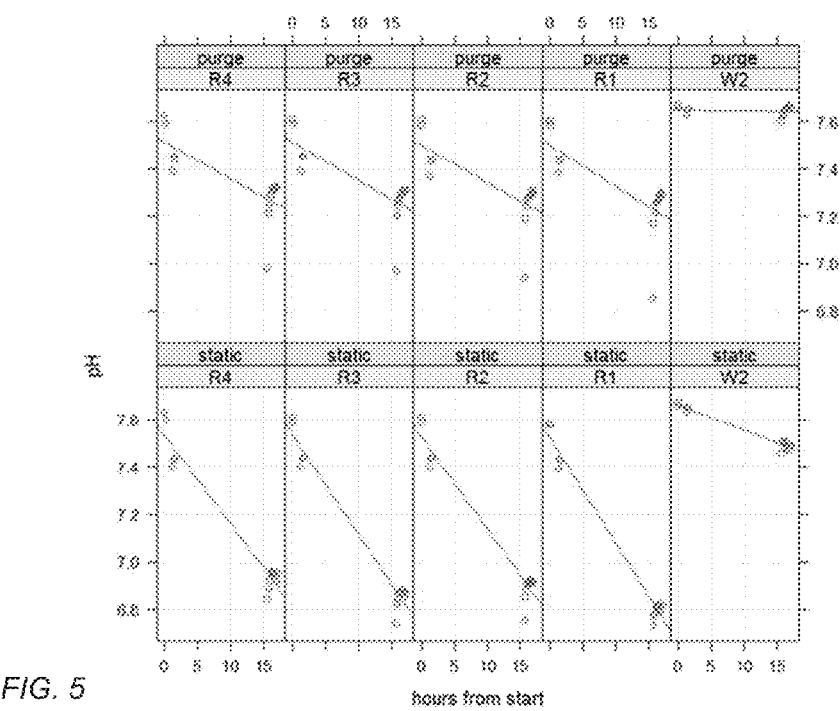
FIG. 5 includes graphs illustrating pH change in reagent solutions.

As illustrated in FIG. 5, the cycled solutions (upper graphs) exhibit a lower change in pH over the 20 hour period than the solutions held at atmospheric pressure (lower graphs). In particular, the nucleotide solutions that undergo cycling change in pH by less than 0.4 units, whereas the nucleotide solutions that are held at atmospheric pressure change by 0.8 pH units. The wash solution that is cycled maintains a near constant pH, whereas the wash solution that is held at atmospheric pressure changes by approximately 0.2 pH units.

In a first aspect, a method of sensing nucleotide reactions includes flowing at least one nucleotide solution from a container of at least two containers of a sensor system. The sensor system includes a sensor sensitive to a byproduct of nucleotide incorporation. Each container of the at least two containers includes a different nucleotide solution. The sensor system enters an idle mode after flowing. The method further includes cycling the at least two containers through at least two cycles. Each cycle includes depressurizing the at least two containers for a first period and pressurizing the at least two containers for a second period. The method also includes pressurizing the at least two containers when the sensor system enters an active mode.

In an example of the first aspect, the first period is at least twice the second period. In another example of the first aspect and the above example, a ratio of the first period to the second period is in a range of 10:1 to 100:1. For example, the ratio is in a range of 15:1 to 75:1.

In a further example of the first aspect and the above example, the sensor system further includes a flow chamber in fluid communication with the at least two containers and further includes a reaction chamber disposed within the flow cell and operatively coupled to the sensor. For example, the reaction chamber has a volume in a range of 0.01 fL to 10 pL.

In an additional example of the first aspect and the above example, the sensor system further includes a template nucleic acid disposed proximal to the sensor.

In another example of the first aspect and the above example, the sensor includes an ion sensitive field effect transistor (ISFET). In a further example of the first aspect and the above example, the byproduct influences pH.

In an additional example of the first aspect and the above example, flowing the at least one nucleotide solution includes flowing through a degasser.

In a second aspect, an apparatus includes at least two containers. Each container of the at least two containers includes a different nucleotide solution. The apparatus further includes a degasser in fluid communication with a container of the at least two containers. The degasser is to receive a nucleotide solution from the container of the at least two containers and is to separate dissolved gas from the nucleotide solution received from the container of the at least two containers. The apparatus further includes a flow chamber in fluid communication with the degasser. A sensor is disposed within the flow chamber. The sensor is sensitive to a byproduct of nucleotide incorporation.

In an example of the second aspect, the sensor includes an ISFET sensor. For example, the ISFET sensor can be disposed within a reaction chamber disposed within the flow chamber. In a further example, the reaction chamber has a volume in a range of 0.01 fL to 10 pL.

In another example of the second aspect and the above examples, the degasser includes a gas permeable tubing in fluid communication with the at least two containers. In an example, the gas permeable tube includes a fluoropolymer.

In a further example of the second aspect and the above examples, the byproduct influences pH.

In an additional example of the second aspect and the above examples, the apparatus further includes a flow control device in fluid communication between the degasser and the flow chamber.

In another example of the second aspect and the above examples, the apparatus further includes a flow control device. The degasser is in fluid communication between the flow control device and the flow chamber.

In a further example of the second aspect and the above examples, the apparatus further includes a vacuum device operatively coupled to the degasser.

In an additional example of the second aspect and the above examples, the apparatus further includes an inert gas system in fluid communication with the at least two containers.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A method to reduce error in detecting nucleotide reactions, the method comprising:
    flowing at least one nucleotide solution from one of at least two containers of a sensor system into an electronic sensor system including a sensor sensitive to detect a byproduct of nucleotide incorporation including pH changes, each container including a different nucleotide solution, the sensor system entering an idle mode after flowing;
    cycling the at least two containers through at least two cycles, each cycle including depressurizing the at least two containers for a first period and pressurizing the at least two containers for a second period; and
    pressurizing the at least two containers when the sensor system enters an active mode.

2. The method of claim 1, wherein the first period is at least twice the second period.

3. The method of claim 1, wherein a ratio of the first period to the second period is in a range of 10:1 to 100:1.

4. The method of claim 3, wherein the ratio is in a range of 15:1 to 75:1.

5. The method of claim 1, wherein the sensor system further includes a flow chamber in fluid communication with the at least two containers and further includes a reaction chamber disposed within the flow cell and operatively coupled to the sensor.

6. The method of claim 5, wherein the reaction chamber has a volume in a range of 0.01 fL to 10 pL.

7. The method of claim 1, wherein the sensor system further includes a template nucleic acid disposed proximal to the sensor.

8. The method of claim 1, wherein the sensor includes an ion sensitive field effect transistor (ISFET).

9. The method of claim 1, wherein the byproduct influences pH.

10. The method of claim 1, wherein flowing the at least one nucleotide solution includes flowing through a degasser.

* * * * *